US006969775B2

United States Patent
Bhattacharya et al.

(10) Patent No.: US 6,969,775 B2
(45) Date of Patent: Nov. 29, 2005

(54) METHOD OF PRODUCING ORGANIC COMPOUNDS IN PRESENCE OF OXYETHYLENE ETHER CATALYST AND IN A SOLVENT MINIMIZED ENVIRONMENT

(75) Inventors: Apurba Bhattacharya, Corpus Christi, TX (US); Gaurang L. Parmar, Kingsville, TX (US); Vikram C. Purohit, College Station, TX (US); Nitin C. Patel, Kingsville, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 10/666,543

(22) Filed: Sep. 19, 2003

(65) Prior Publication Data

US 2004/0138509 A1 Jul. 15, 2004

Related U.S. Application Data

(60) Provisional application No. 60/412,074, filed on Sep. 19, 2002.

(51) Int. Cl.[7] ............................................. C07C 233/05
(52) U.S. Cl. ..................................................... 564/223
(58) Field of Search .......................... 564/223; 568/662, 568/706; 548/490; 544/63

(56) References Cited

FOREIGN PATENT DOCUMENTS

WO            95/15997      *   6/1995

OTHER PUBLICATIONS

Nahmed et al, Tetrahedron Lett, vol. 32(37), pp. 4917–4920 (abstract only).*

* cited by examiner

*Primary Examiner*—Shailendra Kumar
(74) *Attorney, Agent, or Firm*—Locke Liddell & Sapp LLP

(57) ABSTRACT

A process of producing organic compounds, such as acetaminophen, nitroalcohols and indoles, employs a catalyst system of an oxyethylene ether and a metal containing inorganic or organic reagent. The oxyethylene ether at least partially complexes the metal of the inorganic or organic reagent. As such, the reactions may be conducted neat. The processes are environmentally friendly and operationally simple.

7 Claims, No Drawings

METHOD OF PRODUCING ORGANIC COMPOUNDS IN PRESENCE OF OXYETHYLENE ETHER CATALYST AND IN A SOLVENT MINIMIZED ENVIRONMENT

This application claims the benefit of U.S. Provisional Application Ser. No. 60/412,074, filed Sep. 19, 2002.

FIELD OF THE INVENTION

The invention relates to the synthesis of organic compounds in the presence of a catalysis system containing an oxyethylene ether.

BACKGROUND OF THE INVENTION

In the United States, approximately 160 billion gallons of solvents are used each year. Many of these solvents are volatile and are listed in the United States' Clean Air Act as substances to be avoided. The majority of solvents further contribute to depletion of the ozone layer (especially evident with chlorofluourocarbons), are highly toxic (especially chlorinated solvents), are a chief factor in birth defects, and, in addition, are a major cause of fires and explosions.

Over the past few years, significant research has been directed toward the development of new technologies for environmentally benign processes (green chemistry), which are both economically and technologically feasible. An important area of green chemistry deals with solvent minimization.

Solvent minimization processes are those conducted in minimal amount of solvent or are conducted in solvent-free environments. Solvent-free processes always exhibit the greatest efficiency because they eliminate the costs of processing, handling and disposal of the solvent. Limited success has been achieved with solvent minimization processes employing aqueous systems, ionic liquids, immobilized solvents, dendrimers, amphiphilic star polymers or supercritical fluids. The major challenge encountered in solvent minimization processes is the lack of a common phase (typically provided by the solvent medium) which brings the reactants into closer proximity.

Solvent minimization processes are especially desired in the manufacture of certain compounds used as active ingredients in pharmaceuticals. Exemplary of the solvent processes to synthesize N-acetyl-p-aminophenol (APAP or acetaminophen, sold under the trademark Tylenol®) are the Mallinckrodt Process, Celanese Process, Sterling Process and Monsanto Process. Such processes, named after the formulator practicing the process, are summarized below:

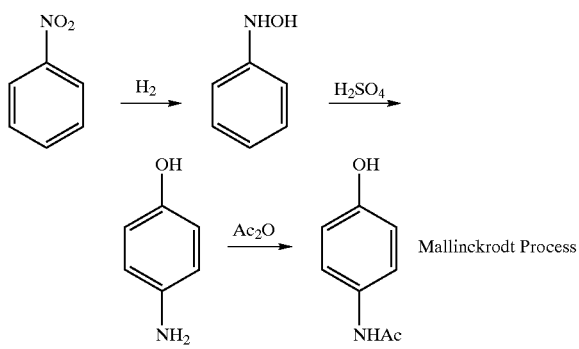

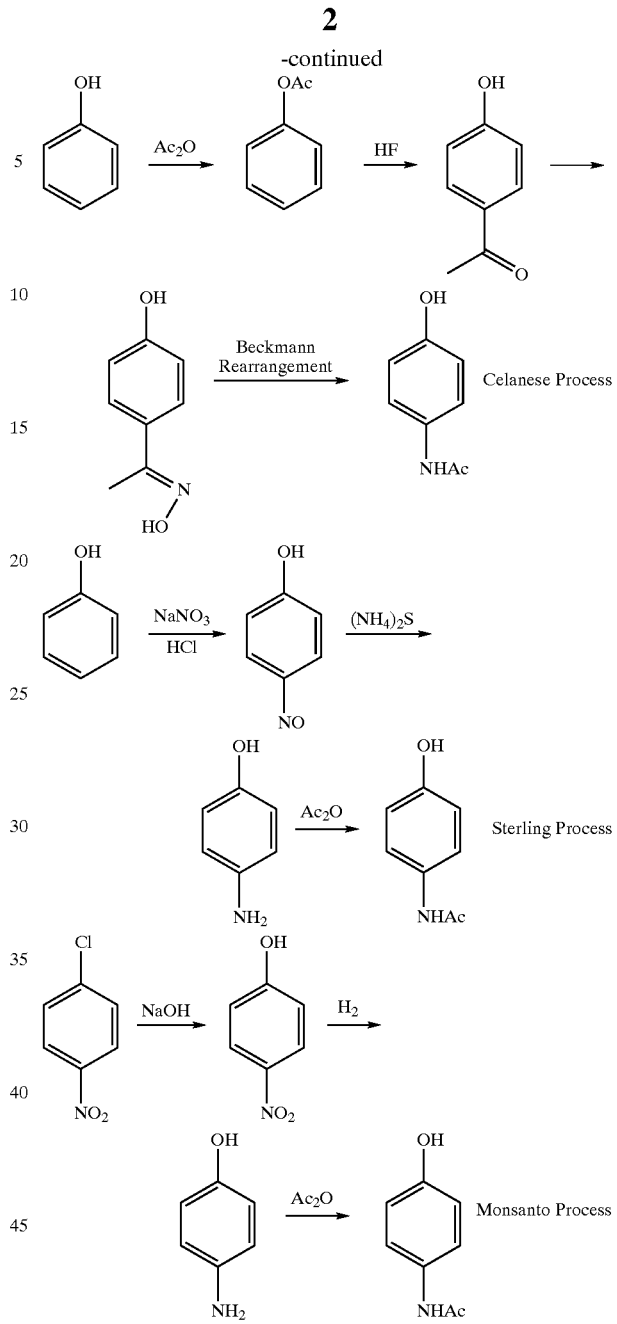

These processes are the subject of numerous patents.

For example, in the Monsanto Process, described in U.S. Pat. Nos. 3,334,587 and 3,076,030, both of which are herein incorporated herein by reference, as well as the Sterling Process, p-nitrophenol is reduced to p-aminophenol which is then acetylated to render N-acetyl-p-aminophenol. The reduction of p-nitrophenol to produce p-aminophenol involves hydrogenating the p-nitrophenol in the presence of a catalyst such as platinum, palladium, nickel, a noble metal, or an oxide of platinum, palladium, or a noble metal. Gaseous hydrogen is commonly used as a reducing agent. The acetylating agent is usually acetic anhydride. The reaction solvent is an inert media such as, for example, acetic acid, water, a water-isopropanol mixture, ethyl acetate,- thiophene-free benzol, or a hydrocarbon. Processes of producing acetyl-p-aminophenol which do not require the isolation and purification of p-aminophenol, which is oxidatively unstable, are highly desirable. Unfortunately, the processes of the prior art require the use of undesirable solvents.

In the Celanese Process, as described in U.S. Pat. No. 4,954,652, incorporated herein by reference, N-acetyl-para-aminophenol is prepared by subjecting 4-hydroxyacetophenone oxime to a Beckman rearrangement in the presence of a thionyl chloride catalyst and an alkyl alkanoate as the reaction solvent. The patent also discloses an integrated process wherein 4-hydroxyacetophenone is reacted with a hydroxyl amine salt and a base to obtain the ketoxime of the ketone, e.g. 4-hydroxyacetophenone oxime, extracting the ketoxime product from the reaction with alkanoate ester and subjecting the ketoxime dissolved in ester to a Beckman rearrangement in the presence of a thionyl catalyst. Like the other processes of the prior art, the Celanese Process requires the use of an organic solvent.

Since acetaminophen is the most prescribed analgesic in the world because of its antipyretic activity, a solvent minimized process is desired.

Solvent based chemistry is also needed in the production of nitroaldols. Nitroalcohols are valuable intermediates for the synthesis of pharmacologically active β-amino alcohols:

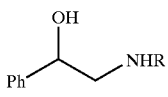

Phenylethanolamine
(Vasoconstrictor)

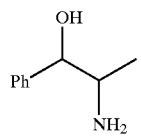

Phenylpropanolamine
(bronchodilator)

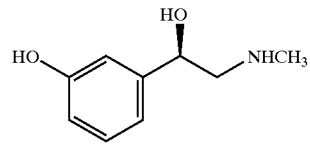

Phenylepinephrine (Mydratic)

Such alcohols are the key elements present in β-blockers and agonists and are highly effective in the treatment of cardiovascular disease, asthma, and glaucoma. Nitroalkenes derived from nitroalcohols possess significant biological activities such as insecticidal, fungicidal, bactericidal, rodent-repellant and antitumor agents and are also utilized for the preparation of a variety of important organic compounds including prostaglandins, pyrroles, porphyrins, as set forth below:

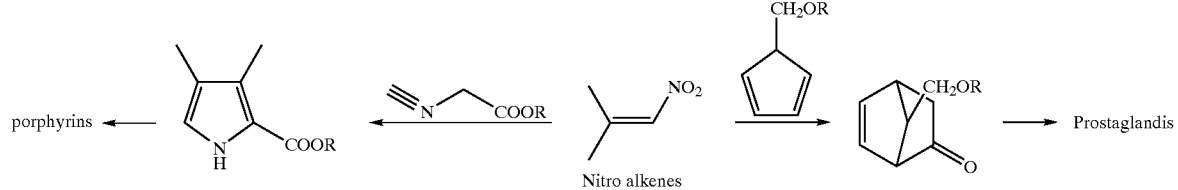

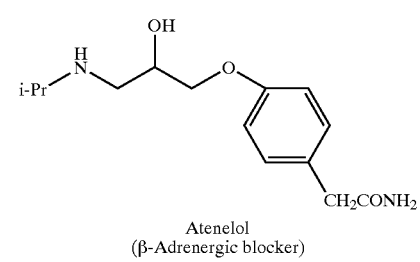

Atenelol
(β-Adrenergic blocker)

Traditional synthesis of nitroalcohols involving the base catalyzed condensation of aldehydes or silyl nitronates with the corresponding nitroalkanes are low yielding (50–60%), prohibitively slow (4–7 days) and waste producing. A synthesis involving potassium fluoride promoted aldol-like condensation of an aldehyde with 1-nitroalkane in polar protic solvent (e.g. isopropanol) has further been reported. Complicated unit operations, poor conversion and disposal of solvents, $CaF_2$, celite, waste layers and salts from aqueous acid base extractions make this process environmentally unattractive. Further, an alternate synthesis of nitro alcohol involving addition of $N_2O_4$ or acylnitrate to an olefin has been proposed:

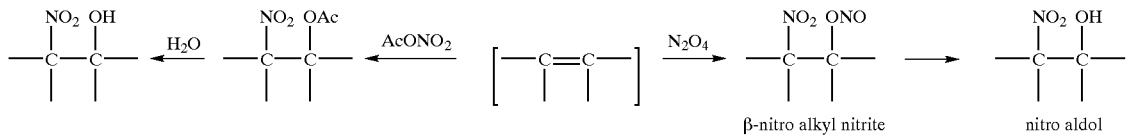

Unfortunately, such synthesis is impractical and costly.

Alternative synthesis have further been sought for the production of oxazinones and thiazoles, including benzothiazoles. Such fused heterocycles are of considerable interest owing to their biological activity. For example, benzooxazin-4-ones (acylanthranils) act as chrymotripsin inactivators, inhibitors of human leukocyte elastase, serin protease and 2-aryl derivatives and have the ability to lower the concentration of plasma cholesterol and triglyceride. Moreover, 2-substituted-4H-3,1-bezoxazin-4-ones have been reported to be used as precursors for the preparation of pharmaceutically active compounds such as antimicrobial agents. See, for instance, Organic Letters, 1, 10, 1619–22, 1999.

Further, heterocycles containing the thiazole moiety are present in many natural products such as bleomycin, epothilone A, lyngbyabellin A and dolastatin 10. Benzothiazole derivatives are of particular interest in light of their antimicrobial properties and applications in industry as antioxidants and vulcanization accelerators.

Therefore, a need exists for the development of a synthesis of organic compounds, including nitroalcohols, acetaminophen, indoles, thiazoles and oxazinones, using an efficient catalytic method in a solvent minimized environment.

SUMMARY OF THE INVENTION

The present invention provides a novel method for producing an organic compound in the substantial absence of an organic solvent. The reaction is conducted in the presence of a catalyst system. The catalyst system includes an oxyethylene ether, such as polyethylene glycol or an aryl polyoxyethylene ether of the formula:

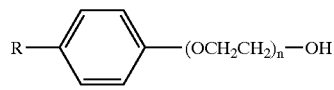

(I)

wherein R is an aryl, alkyl or aralkyl group having from 1 to 20 carbon atoms and n has an average value between from about 9 to about 150.

In the method of the invention, at least one organic reactant is brought into contact with at least one inorganic or organic metal reagent in the presence of the oxyethylene ether. The inorganic or organic metal reagent may further function as a co-catalyst. The reaction is conducted until the oxyethylene ether at least partially complexes the metal of the inorganic or organic metal reagent.

By using catalytic amounts of surfactant compounds, it is possible to synthesize the target organic compound in a solvent minimized environment.

In a preferred embodiment, acetaminophen, nitrodaldols, indoles, oxazinones and thiazoles may be produced in a solvent-free environment.

Acetaminophen may be produced by a one step amidation/reduction of a nitro aromatic compound of the formula:

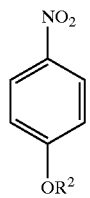

(II)

wherein $R^2$ is —H or a $C_1$–$C_4$ alkyl group, with an alkali metal thioacetate wherein a neutral ether cleavage reaction under nucleophilic conditions occurs such that the $NO_2$- group is readily converted to —NHCOCH$_3$ in a one step transformation.

This process constitutes the shortest synthesis of acetaminophen utilizing the inexpensive commodity chemical p-nitrophenol. The acetamidation reaction of the invention successfully convert p-nitrophenol to acetaminophen in >90% yield.

Where $R_2$ is a $C_1$–$C_4$ alkyl group, treatment of the compound of formula (II) with alkali metal thioacetate (1 eq) in the presence of the oxyethylene ether produces p-nitrophenol by selective cleavage of the alkoxy group. The same reaction utilizing a higher molar amount of alkali metal thioacetate (3 eq) produces a reduction of the nitro group to acetamido group.

The process of the invention may further be used to produce nitroalcohols that are useful synthetic intermediates for a variety of amino alcohols utilized as β-adrenergic blockers, bronchodialators and vasoconstrictors. The reaction is performed neat and little work-up is necessary. The reaction proceeds to near quantitative conversions with about 100% overall efficiency and is practical and economically attractive. Crown ether type selective complexation of metal ions also allows adjustment of the process to make it substrate/reagent selective.

The method of the invention may further be applied to the production of indoles, oxazinones and thiazoles.

DETAILED DESCRIPTION OF THE INVENTION

The invention relates to a method for producing an organic compound that is traditionally made by a process wherein an inorganic metallic serves as the catalyst. The method of the invention proceeds neat, in a solvent minimized environment, under homogeneous or heterogeneous conditions and in the presence of a catalytic amount of an oxyethylene ether.

In one aspect of the invention, the process employs a dual catalytic system whereby the oxyethylene ether is used in conjunction with the traditional metal catalyst. The oxyethylene ether offers the capability to increase liquid-liquid interface area. In addition, it enables selective complexation of metal ions, thereby resulting in solubilization of the traditional metal catalyst in the oxyethylene ether media.

The resulting product can be separated from the catalyst by simple filtration (specifically for heterogeneous reactions) without any exhaustive work-up, rendering the process simple and relatively waste-free. Since a solvent minimized environment is used, the throughput (space-time yield) is higher, resulting in an extremely efficient and economic process.

The present invention thus provides a process for synthesizing organic compounds in a solvent minimized environment by using catalytic amounts of oxyethylene ether compounds. The term "solvent minimized" is a functional term and is meant to include those reactions which use either no traditional solvent or such a minimal amount that the solvent would not function as a significant or controlling part of the reaction. Preferably, the solvent minimized environment has an amount of solvent no greater than trace amounts of solvent in the reaction, that is essentially "solvent free".

In a preferred embodiment, the invention relates to the solvent-free production of nitroalcohols or the one-step transformation of a —$NO_2$ to —NHCOR to render acetaminophen. Further, the amidation process of the invention includes a one-step process of producing an indole, thiazole (including a benzothiazole) or oxazinone from a nitro containing aromatic compound. By proper choice of the catalyst, base and reaction conditions, reactions can be performed to a level of practical conversion and selectivity.

Preferred oxyethylene ethers include polyethylene glycol as well as an aryl polyoxyethylene ether of the formula:

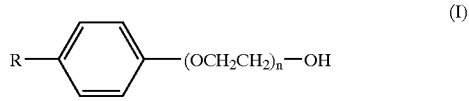

(I)

wherein R is an aryl, alkyl or aralkyl group having from 1 to 20 carbon atoms and n has an average value between from about 9 to about 150, preferably an average value between from about 9 to about 70, more preferably an average value between from about 16 to about 40.

Especially preferred as the polyoxyethylene ether are those of the family octylphenoxypolyethoxyethanol, commercially available and sold under the name Triton X-100, wherein n of formula (I) is about 9 to about 9.5, as well as TRITON X-405, wherein n is about 40 or 41.

It is believed that the oxyethylene ether functions as a co-catalyst with the inorganic or organic metal containing reagent such that the ether moiety of the oxyethylene ether (polyether moiety where the oxyethylene ether is an aryl polyoxyethylene ether) complexes the metal ion of the inorganic or organic metal containing reagent (analogous to crown ether of the base), thereby solubilizing the inorganic or organic metal containing reagent in the organic environment.

The synthesis of nitroaldols consists of condensation of a $C_1$–$C_{20}$ alkyl or aromatic aldehyde, such as propionaldehyde, with a $C_1$–$C_{20}$ 1-nitroalkane, optionally substituted with an aromatic ring, such as nitropropane, in the presence of the dual catalytic system of the invention. The reaction is performed neat.

The inorganic metal reagent, used as co-catalyst, serves as an inorganic base and is preferably an alkali, alkaline earth, or metal inorganic hydroxide, such as KOH or polymeric hydroxide ion exchange resins.

The oxyethylene ether portion of PEG or the polyoxyethylene unit of the aryl polyoxyethylene ether is capable of complexing the metal ion (analogous to crown ether of the base), thereby solubilizing the base in the organic environment. The oxyethylene ether units may further catalyze the reaction by increasing the liquid-liquid interface.

Schematically the nitroadol synthesis of the invention may be represented as follows:

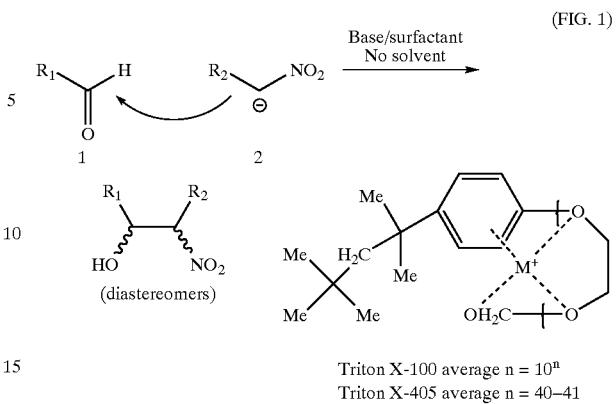

(FIG. 1)

Triton X-100 average n = $10^n$
Triton X-405 average n = 40–41 wherein $R_1$ is a $C_1$–$C_{20}$ alkyl or aromatic group and $R_2$ is a $C_1$–$C_{20}$ alkyl group, optionally substituted with one or more aromatic rings. Since the reaction is performed neat, the (nitroalcohol) product is directly obtained and is ready to be utilized for the next step in a synthetic sequence. No work up is necessary. Overall throughput of the reaction is 100%. Environmentally unfriendly reagents are further replaced with the inexpensive base, such as KOH.

Preferred results are exhibited where the nitroalkane is nitropropane and the aldehyde is propionaldehyde utilizing Triton X-100 as the catalyst and an alkali metal, alkaline earth or tetraalkyl ammonium hydroxide or alkali acetate as the inorganic or organic metal reagent (>90% after 3 h). The alkyl group of the tetralkyl ammonium hydroxide is preferably a $C_1$–$C_4$ alkyl group. Triton X-405 is also especially preferred with K, Li and Cs hydroxides. The topology of the Triton X/ethylene glycol units is believed to be responsible for preferential complexation of metal ions analogous to crown ether complexation of metal ions. Polyethylene glycol (uncapped) and polyethylene glycol dimethyl ether (capped) were also especially preferred when used in conjunction with KOH as base (>90% after 3 h).

The oxyethylene ether is utilized in a catalytic amount, generally ranging between from about 0.1 g or less to about 20 g per 100 g of the organic reactant.

The solvent minimized amidation process of the invention may further apply to the synthesis of actaminophen, as illustrated in the following reaction scheme:

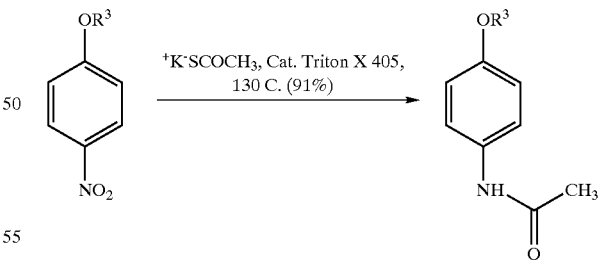

wherein $R^3$ is —H or a $C_1$–$C_4$ alkyl group. The thioacetate is shown to be potassium thioacetate, though any alkali metal thioacetate may be acceptable. The oxyethylene ether is preferably a Triton, such as Triton X-405. Treatment of p-nitroanisole with potassium thioacetate (1 eq) as a nucleophile and Triton-X, as catalyst, renders p-nitrophenol via neculeophilic cleavage of the —OMe group. The same reaction, when conducted utilizing higher molar amount of potassium thioacetate (3 eq) under otherwise identical conditions, renders conversion of the nitro group to an acetamido group; the —OMe group remaining intact under such conditions. Acetamidation by converting p-nitrophenol to p-hydroxyacetamide renders an approximately 90% yield.

The process further involves the solubilization of acetaminophen in a dilute inorganic acid, such as HCl, filtration and distillative removal of water.

The method of the invention may also be employed in the synthesis of heterocyclic compounds, such as indoles, from nitro-substituted aromatic compounds. Indole alkaloids have important physiological activity. For example, trytophan, an essential amino acid, is a constituent of many proteins and further serves as a biosynthetic precursor for a wide variety of tryptamine- and indole-containing secondary metabolites. The synthetic route to the indoles takes advantage of the novel amidation of the nitro functionality and is depicted below. Strategic manipulation of the functional groups in appropriate positions permits the production of a variety of substituted indoles and aza indoles.

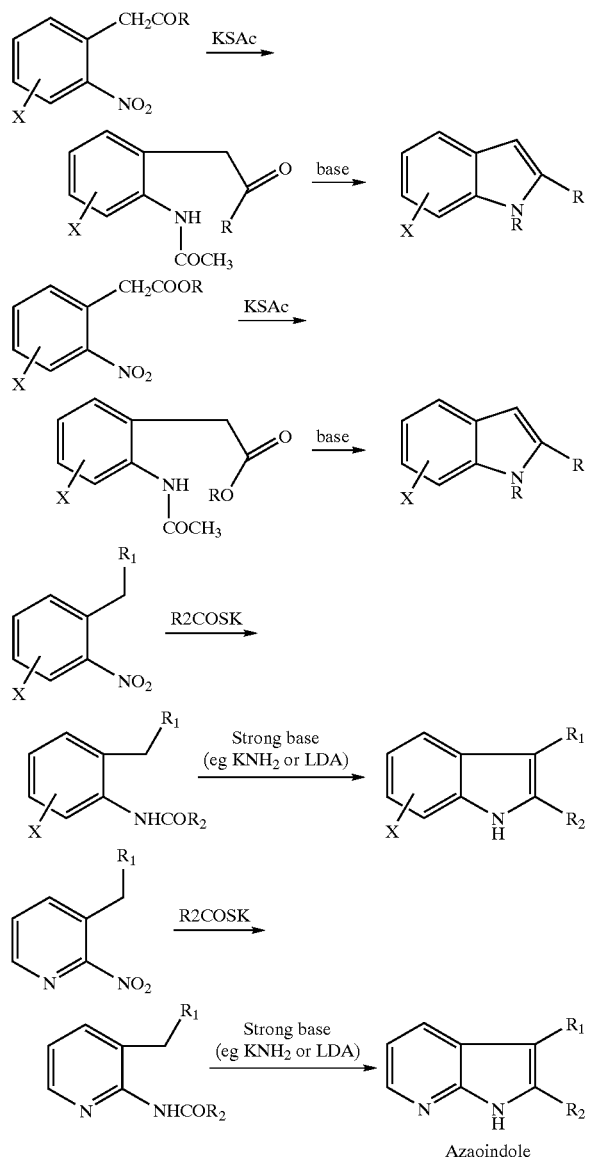

Azaoindole

The existing Leimgruber-Batcho synthesis of indoles suffers from the reduction of the enamine intermediate during the reduction of the $NO_2$ functionality. Replacing existing $TiCl_3$ with thioacetate in the reduction step circumvents that problem.

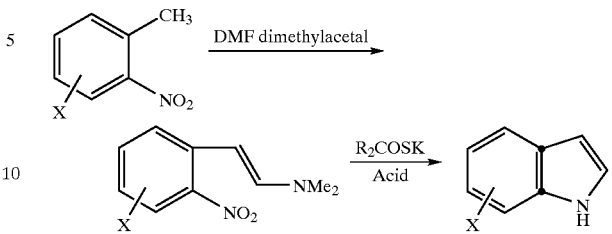

Further, the solvent minimized amidation process of the invention may be used to produce oxazinones as well as thiazoles. For instance, an aryl O-nitrobenzoate ester can undergo alkali metal thioacetate mediated amidation (of the $-NO_2$ functionality). Concomitant cyclization of the amide through the ester linkage gives rise to the corresponding oxazinone. Thus, treatment of 2-nitrobenzoic acid methyl ester with potassium thioacetate in presence of catalytic amount of Triton X-405 has been demonstrated to produce cleanly the 2-methyl-benzo[d][1,3]oxazin-4-one as a major product in accordance with the following schematic:

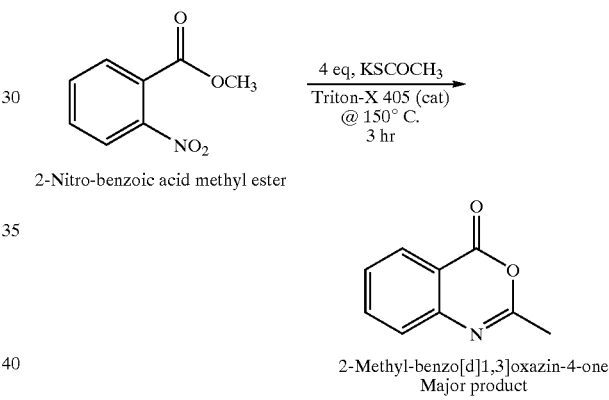

2-Nitro-benzoic acid methyl ester

2-Methyl-benzo[d]1,3]oxazin-4-one
Major product

Treatment of the O-nitrobenzoate ester with three equivalents potassium thioacetate at 130° C. rendered 2-methyl benzothiazole as the exclusive product. No benzooxazinone was formed. The product formation is attributable to thioacetate mediated hydrolysis, decarboxylation of the corresponding carboxylate anion (activated by the $O-NO_2$ functionality), followed by nucleophilic addition of the thioacetate anion and concomitant cyclization through the amide functionality. A representative schematic is set forth below:

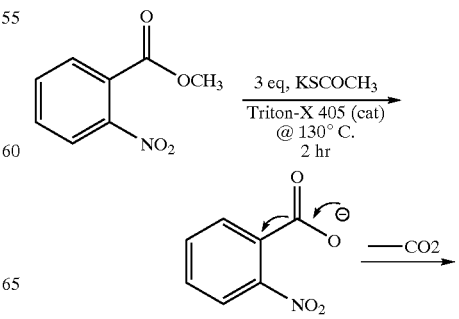

-continued

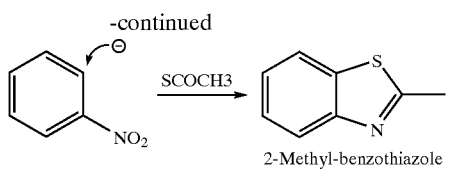
2-Methyl-benzothiazole

Alternatively, benzothiazole can also be produced by the action of the alkali metal thioacetate and oxyethylene ether on the O-bromobenzoate. Reduction of the —NO$_2$ group followed by nucleophilic displacement of the aryl bromide and concomitant cyclization of the —NH$_2$ through the thioacetate function cleanly renders the 2-methyl bezothiazole in high yield, as set forth below:

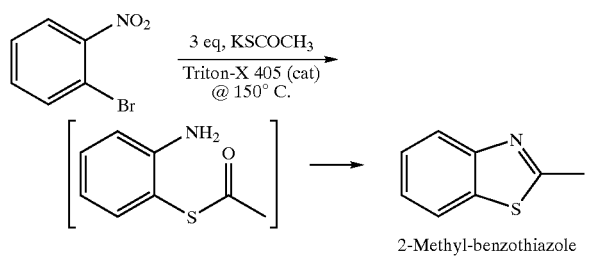
2-Methyl-benzothiazole

The following non-limiting examples, and comparative demonstrations, bring out the more salient features of the invention. All parts are given in terms of weight units except as may otherwise be indicated.

EXAMPLES

Example 1

Synthesis of Acetaminophen

This Example illustrates the shortest synthesis of acetaminophen known to date and uses a solvent minimized environment as a one-step amidation/reduction. The Triton X-405 catalyst was heated for half an hour at 130° C. to remove water and then a quantity of potassium thioacetate was added with mixing. Then, one equivalents of p-nitrophenol was added with mixing; all the while maintaining the reaction mixture at 130° C. The progress of the reaction was followed by HPLC analysis using 1:1 acetonitrile:water or solvent at a flow rate of 1 ml/min.

The p-nitrophenol appeared at a 3.3 minute peak and product "p-hydroxy-acetanilide" appeared at a 1.1 minute peak. Complete disappearance of the starting material occurred in 3.0 hours with the 2.5 hours trace showing 75% "p-hydroxy-acetanilide." The reaction mixture was then cooled down to room temperature.

The reaction sequence and the results are presented below:

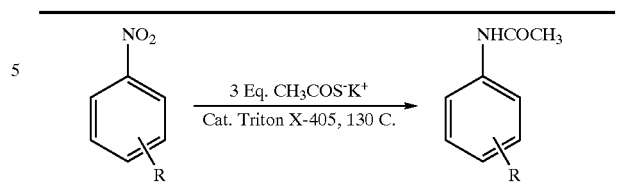

| Run No. | R | Percent Conversion | Time (hrs) |
|---|---|---|---|
| 1 | 4-CH3 | 94 | 2 |
| 2 | 3-CH3 | 96 | 2 |
| 3 | 4-O-Phen | 88 | 2.5 |
| 4 | 4-Phen | 88 | 2.5 |
| 5 | 4-O-CH3 | 80 | 2.5 |
| 6 | 3-O-CH3 | 80 | 3 |
| 7 | 3-OH | 88 | 3 |
| 8 | 4-OH | 88 | 3 |
| 9 | H | 94 | 2 |

The resultant reaction mixture was dissolved in acidified water of pH 2.0. To this charcoal was added take care of sulfur. The above mixture was then mixed and filtered. The filtrate was dried in a rotary vacuum. Upon drying the filtrate, p-hydroxy acetanilide or acetaminophen appeared as white crystals; the yield was about 80%.

In addition to the solvent-free reaction, which used a catalytic amount of Triton X-405, a solvent based reaction was also conducted using dimethyl formamide as solvent. The results were comparable to those of the solvent-free compound.

Example 2

Amidations and Reduction Involving Cleavage of Alkyl Group

An exemplary schematic representation of the chemical reaction is set forth below:

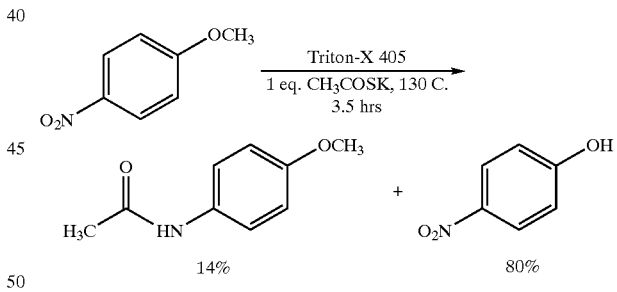

wherein potassium thioacetate is used to cleave a methyl group and reduce a nitro group. Potassium thioacetate can selectively cleave the methyl group from methoxy ether as well as reduce the nitro group to an acetamino group when a higher molar amount of potassium thioacetate is used.

The reaction was carried out using Triton X-405 in a catalytic amount. A catalytic amount of Triton X-405 was heated at 130° C. for half an hour to remove water and to this a quantity of potassium thioacetate was added with mixing and then one equivalence of p-nitroanisole was added with mixing, all the while maintaining the reaction mixture at 130° C.

The progress of the reaction was followed by HPLC analysis using 1:1 acetonitrile:water as the solvent at a flow rate of 1 ml/min and UV detection at 254 nm. The product p-methoxy acetanilide and p-nitrophenol appeared as peaks at 2.2 min and 3.3 min, respectively. Complete disappearance of the starting material occurred in 4 hours with 3.5 hour HPLC. A trace showing p-methoxy acetanilide was formed in 14% yield and p-nitrophenol formed in 80% yield.

In a similar reaction, but using 3 equivalents of potassium thioacetate, a 90% yield of p-methoxy-acetanilide and a trace of p-nitrophenol which is about 10%. The identity of the products was determined by GC/mass spectral analysis.

Example 3

Complexation Study on Oxyethylene Ether

The Triton-X/base combination plays an important role in the rate of the nitroaldol reaction. (As used herein, "base" refers to the inorganic or organic metal containing reagent.) For example, reacting nitropropane with propionaldehyde, utilizing Triton-X-100 as the catalyst, KOH and CsOH were found to be the most effective bases (>90% after 3 h), whereas reactions were slower with LiOH, NaOH and tetrabutyl ammonium hydroxide (approximately 30% completion after 3 hours). No reaction was observed with Ba and Ca or Mg-hydroxide in conjunction with Triton X-100. Triton X-405 was also effective with K, Li and Cs hydroxides. The topology of the Triton-X/ethylene glycol units is believed to be responsible for preferential complexation of metal ions analogous to crown ether complexation of metal ions. In line with these observations, polyethylene glycol (uncapped) and polyethylene glycol dimethyl ether (capped) were also effective when used in conjunction with KOH as base (>90% after 3 h). Particularly noteworthy is the fact that in the presence of potassium acetate as base, nitropropane underwent smooth condensation with propionaldehyde (>95% after 20 hours at 60–65° C.) utilizing Triton X-100 as oxyethylene ether. Triton X-405, PEG and PEG dimethyl ether were also equally effective with KOAc.

The complementary nature of the various types of Triton-X and specific counterions in the organic medium might originate from crown ether like metal ion recongnition by the polyether cavity of Triton-X. Control experiments performed by adding 1 g KOH (as a representative hydroxide base) to 100 mL toluene (as a representative organic solvent) showed no dissolution of KOH in the organic layer. Adding Triton-X 405 (1 g) to this mixture showed significant dissolution of KOH in the toluene layer. Using different metal hydroxide base/Triton-X combination followed by titration of the amount of base transferred to the toluene layer (with standardized 0.001 N HCl) allowed us to quantify the solubilization effect and hence the extent of $M^+$ ion/surfactant complexation. The titration results are summarized in Table 1.

TABLE 1

Extent of dissolution of metal hydroxide [M(OH)x] in toluene

| Run | Base [M(OH)x] | Surfactant | Amount (in mL) of 0.001 N HCl needed for titration end point |
|---|---|---|---|
| 1 | none | Triton-X100 (average 10 PEG units) | 0[1] |
| 2 | none | Triton-X405 (average 40 PEG units) | 0 |
| 3 | KOH | Triton-X100 | 7.0 |
| 4 | KOH | Triton-X405 | 76.4 |
| 5 | KOH | Triton-X405 red. (the aromatic ring reduced) | 31 |

TABLE 1-continued

Extent of dissolution of metal hydroxide [M(OH)x] in toluene

| Run | Base [M(OH)x] | Surfactant | Amount (in mL) of 0.001 N HCl needed for titration end point |
|---|---|---|---|
| 6 | KOH | PEG [MW: ca 4600] uncapped | 29 |
| 7 | KOH | PEG Dimethyl ether [MW: ca 250] | 23 |
| 8 | KOH | Igepal DM-970 Dinonylphenyl Ether (average 150 PEG unit) | 2 |
| 9 | KOH | Igepal CO-990 Nonylphenyl Ether (average 100 PEG unit) | 3 |
| 10 | NaOH | Triton-X100 | 7.5 |
| 11 | NaOH | Triton-X405 | 6.1 |
| 12 | $Ca(OH)_2$ | Triton-X100 | 0 |
| 13 | $Ca(OH)_2$ | Triton-X405 | 0 |
| 14 | $Mg(OH)_2$ | Triton-X100 | 0 |
| 15 | $Mg(OH)_2$ | Triton-X405 | 0 |
| 16 | CsOH | Triton-X100 | 18 |
| 17 | CsOH | Triton-X405 | 780[2] |

[1]In absence of surfactant no dissolution of base was detected.
[2]Control experiments indicated that CsOH is partially soluble in toluene even in absence of surfactant.

The extent of complexation of $K^+$ ion is concluded to be a function of the type of oxyethylene ether (number of oxyethylene ether units) used (Runs 1–9). Triton X-405 is a better candidate for complexation of $K^+$ ion. $Mg(OH)_2$ and $Ca(OH)_2$ failed to catalyze the nitro-aldol reaction that is in line with the values obtained for Mg and Ca (Runs 14–17). The surfactant-specific complexation of metal ions in organic medium is akin to cavity selective complexation that exists between crown ethers and metal ions. Because of its cost prohibitive nature, crown ethers are unacceptable for commercial processes, but Triton-X type surfactants could conceivably be used for such processes because of their ready availability and low cost. Crown ether type selective complexation of metal ions further permits adjustment of the process to make it substrate/reagent selective.

Example 4

Preparation of Nitroalcohols

This Example illustrates a means to verify the identity of the products, 2-methyl-4-nitro-hexan-3-ol and 4-nitro-1-phenyl-hex-1-en-3-ol. Such identification was by 1- and 2-dimensional NMR spectroscopy and LC or GC/MS.

Reactions were carried out under an atmosphere of nitrogen and were stirred magnetically unless otherwise noted. All the materials (reagent grade) were purchased from commercial suppliers and were used without purification. Analytical high performance liquid chromatography (HPLC) was carried out by using a Waters 501 pump, Waters Millipore Gradient Controller (Automated), Thermoseparation Products Refractomonitor IV, and Hitachi L 4000 variable wavelength detector.

All NMR spectra were recorded on Bruker, Avance DPX 300 instrument and a 60 MHz Jeol. All the compounds were dissolved in deuterochloroform ($CDCl_3$) for NMR analysis with the proton chemical shift referenced to residual $CHCl_3$ at 7.27 ppm and carbon chemical shift referenced to $CDCl_3$ at 77.0 ppm.

The fully characterized $^1H$ and $^{13}C$ NMR spectrum of 2-methyl-4-nitro-hexan-3-ol and 4-nitro-1-phenyl-hex-1-en-3-ol served as a model for the interpretation of the other analogs. For the identification of the subsequent analogs, the GC or LC/MS was analyzed for the appropriate mass and the $^1H$ and $^{13}C$ NMR spectrum was analyzed for the appropriate chemical shifts and coupling pattern. The following abbreviations are used to report NMR data: s=singlet, d=doublet, t=triplet, q=quartet, b=broad, and m=multiplet. The LC/MS data were acquired using a Shimadzu SCL-10AD VP HPLC chromatograph equipped with a Waters Micromass ZQ mass spectrometer. The GC-MS data was collected using a Hewlett Packard HP 6890 series GC system with a Hewlett Packard 5973 mass selective detector. The melting points were determined using a Thomas-Hoover capillary melting point apparatus and were uncorrected.

n-Propionaldehyde (3.67 g, 57 mmol) was added via a syringe to a stirred mixture of 1-ntiropropane (5 g, 56 mmol), aqueous KOH (60 mg of saturated aqueous solution) and Triton X-405 (60 mg) kept at 60° C. over a period of 30 minutes. The reaction mixture was stirred at 60° C. for 1.5 h at the end of which complete disappearance of starting material and the formation of the two diastereomeric nitroalchol products were observed by HPLC analysis. The following isocratic reverse phase HPLC procedure was used: mobile phase 50/50 Acetonitrile/Water (0.1% phosphoric acid), 4.6 mm×25 cm Altech Hypersil ODS ($C_{18}$) column, and 0.8 ml/min flow rate. The retention times of the reaction mixture species are: n-Propionaldehyde: 6.1 min, 1-nitropropane: 8.20 min, syn-4-Nitro-hexan-3-ol: 8.03 min, and anti 4-Nitro-hexan-3-ol: 7.52 min.

The reaction mixture was cooled to 22° C., and volatile impurities (e.g. trace of un-reacted starting material) were removed under reduced pressure. The mixture was filtered through a cotton plug (to remove any suspended impurities) producing 7.67 g (93% yield) of the two diastereomeric nitroalchols (1.5:1 ratio of anti: syn).

3-Nitro-butan-2-ol. (1) $^1H$ NMR ($CDCl_3$) diastereomer A 60% δ=4.47 (1H, m), 4.11 (1H, m), 3.00 (OH, bs), 1.50 (3, d, J=6.7 Hz), 1.24 (3, d, J=6.7 Hz), diastereomer B 40% δ=4.47 (1H, m), 4.31 (1H, m), 3.00 (OH, bs), 1.53 (3H, d, J=6.7 Hz), 1.22 (3H, d, J=6.7 Hz); $^{13}CNMR$ ($CDCl_3$) δ=87.56, 68.70, 18.58, 14.16; MS 120 ($M^++1$), 119 ($M^+$).

3-Nitro-pentan-2-ol. (2). $^1H$ NMR ($CDCl_3$) diastereomer A 60% δ=4.33 (1H, m), 4.12 (1H, m), 2.76 (1H, OH, bs), 1.93 (2H, m), 1.26 (3H, d, J=6.2 Hz), 0.96 (3H, t, J=7.0 Hz), diastereomer B 40% δ=4.33 (1H, m), 4.12 (1H, m), 2.76 (1H, OH, bs), 1.93 (2H, m), 1.24 (3H, d, J=6.2 Hz), 0.98 (3H, t, J=7.1 Hz); $^{13}CNMR$ ($CDCl_3$) δ=96.13, 68.35, 24.13, 20.08, 10.46; MS 134 ($M^++1$).

2-Nitro-pentan-3-ol (3) $^1H$ NMR ($CDCl_3$) diastereomer A 50% δ=4.49 (1H, m), 4.04 (1H, dt, J=3.3 Hz, 6.3 Hz), 3.06 (1H, OH, bs), 1.56 (1H, m), 1.39 (1H, m), 1.49 (3H, d, J=6.7 Hz), 0.96 (3H, t, J=7.4 Hz), diastereomer B 50% δ=4.49 (1H, m), 3.80 (1H, dt, J=3.4 Hz, 8.0 Hz), 3.06 (1H, OH, bs), 1.39 (2H, m), 1.49 (3H, d, J=6.7 Hz), 0.96 (3H, t, J=7.4 Hz); $^{13}CNMR$ ($CDCl_3$) δ=86.53, 75.33, 26.56, 13.06, 9.72; MS 134 ($M^++1$).

4-Nitro-hexan-3-ol. (4). $^1H$ NMR ($CDCl_3$) diastereomer A 60% δ=4.34 (1H, m), 3.83 (1H, m), 2.73 (OH, bs), 2.15–1.75 (2H, m), 1.70–1.35 (2H, m), 1.00 (3H, t, J=7.4 Hz), 0.95 (3H, t, J=7.4 Hz), diastereomer B 40% δ=4.39 (1H, m), 3.91 (1H, m), 2.73 (OH, bs), 2.15–1.75 (2H, m), 1.70–1.35 (2H, m), 0.99 (3H, t, J=7.4 Hz), 0.96 (3H, t, J=7.4 Hz); $^{13}CNMR$ ($CDCl_3$) δ=94.08, 73.49, 26.75, 21.66, 11.11, 10.32; MS 148 ($M^++1$), 147 ($M^+$).

4-Nitro-heptan-3-ol (5). $^1H$ NMR ($CDCl_3$) δ=4.83 (1H, m); 3.85 (m, 1H), 3.20 (m, 1H), 2.10 (s, 1H), 1.90 (m, 2H), 1.5 (m, 2H), 0.95 (m, 6H); $^{13}CNMR$ ($CDCl_3$) δ=88.22, 72.75, 33.7, 27.05, 18.98, 13.25,7.0; MS 162 (M+1)

5-Nitro-octan-4-ol (6) $^1H$ NMR ($CDCl_3$) diastereomer A 60% δ=4.39 (1H, m); 3.89 (1H, m); 1.99 (2H, m); 1.74 (1H, m); 1.41 (5H, m); 0.97 (3H, t, J=7.3 Hz); 0.96 (3H, t, J=7.3 Hz), $^1H$ NMR ($CDCl_3$) diastereomer B 40% δ=4.47 (1H, m); 4.02 (1H, dt, J=4.0 Hz, 8.3 Hz); 1.99 (2H, m); 1.74 (1H, m); 1.41 (5H, m); 0.97 (3H, m); 0.96 (3H, m); $^{13}CNMR$ ($CDCl_3$) δ=93.15, 72.23, 35.96, 35.59, 19.23, 18.87, 14.10, 13.64; MS 176 ($M^++1$).

3-Nitro-heptan-4-ol (7). $^1H$ NMR ($CDCl_3$) diastereomer A 60% δ=4.39 (1H, m), 3.95 (1H, m), 2.8 (1H, OH, bs), 2.06 (2H, m), 1.89 (1H, m), 1.46 (3H, m), 0.97 (6H, m), diastereomer B 40% δ=4.39 (1H, m), 4.03 (1H, m), 2.8 (OH, bs), 2.06 (2H, m), 1.89 (1H, m), 1.46 (3H, m), 0.97 (6H, m); $^{13}CNMR$ ($CDCl_3$) δ=94.37, 71.98, 35.86, 21.94, 18.58, 13.99, 10.52; MS 162 ($M^++1$)

4-Nitro-1-phenyl-hexan-3-ol (8). $^1H$ NMR ($CDCl_3$) diastereomer A 60% δ=7.40–7.15 (5H, m), 4.41 (1H, m), 3.90 (1H, m), 2.6–3.0 (2H, m), 2.17 (1H, OH, d, J=7.7 Hz), 2.09 (2H, m), 1.83 (2H, m), 0.98 (3H, t, J=7.4 Hz), $^1H$ NMR ($CDCl_3$) diastereomer B 40% δ=7.40–7.15 (5H, m), 4.41 (1H, m), 4.05 (1H, m), 2.6–3.0 (2H, m), 2.40 (1H, OH, d, J=4.0 Hz), 2.09 (2H, m), 1.83 (2H, m), 1.00 (3H, t, J=7.3 Hz); $^{13}CNMR$ ($CDCl_3$) δ=141.19, 129.00, 128.73, 126.65, 94.3,71.7, 35.3, 21.89, 10.75; MS 224 ($M^++1$). mp 41° C.

4-Nitro-1-phenyl-hex-1-en-3-ol (9). $^1H$ NMR ($CDCl_3$) δ=7.45(m, 5H), 6.7(m, 1H), 6.175(m, 1H), 4.66(m, 1H), 4.525(m, 1H), 3.63(s, 1H), 1.75(m, 2H), 0.99(t, 3H); $^{13}CNMR$ ($CDCl_3$) δ=136.07, 129.52, 129.13, 128.89, 128.72, 95.30, 77.97, 24.30, 10.98; LCMS m/z 222.18 ($M^++1$). mp 41° C. (dec.).

2-Methyl-4-nitro-hexan-3-ol.(10). $^1H$ NMR diastereomer A=4.5 (1H, m), 3.68 (1H, dd, J=5.1 Hz, 6.8 Hz), 2.10 (1H, m), 1.73 (2H, m), 1.02–0.90 (9H, m), diastereomer B=4.5 (1H, m), 3.75 (1H, t, J=5.5 Hz), 1.95 (1H, m), 1.83 (2H, m), 1.02–0.90 (9H, m); $^{13}CNMR$ ($CDCl_3$) δ=92.33, 76.70, 30.88, 24.2, 20.01, 16.24, 10.50; MS 162 ($M^++1$), 161($M^+$).

Example 5

Cleavage of Ether

This example is directed to cleavage of ethers in a solvent based and a solvent minimized environment. Formation of ethers and their subsequent cleavage constitute an important method in organic synthesis. Ether cleavage involves harsh conditions (strong acid e.g. $BBr_3$, HBr, $AlCl_3$, molten Pyr, HCl or base e.g. NaHS, NaOR, $NaNH_2$), environmentally unacceptable reagents and is incompatible to acid/base sensitive substrates. Therefore ether cleavage under near neutral conditions is highly desirable. This Example illustrates that the invention can be used for ether cleavage under neutral conditions by treatment with KSCN or $KNO_2$ as nucleophile in a solvent minimized environment (from about 100° C. to about 130° C.). Cleavages of p-nitroanisole was faster than m-nitroanisole (and hence as a lower E act) presumably due to the electron withdrawing resonance of the p-$NO_2$ group. Surfactant mediated solvent-free conditions were also successfully applied to the neutral ether cleavage reactions. Thus a variety of aromatic ethers were cleaved in good to excellent yields by treatment with $KNO_2$ or KSCN as nucleophile in presence of catalytic amounts of Triton X at 160° C.

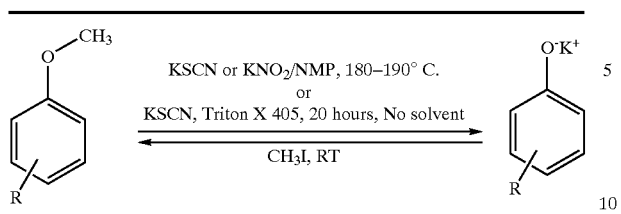

R = p-Nitro, m-Nitro, 4-Cyano, 3,5 Dichlor, 4-CHO

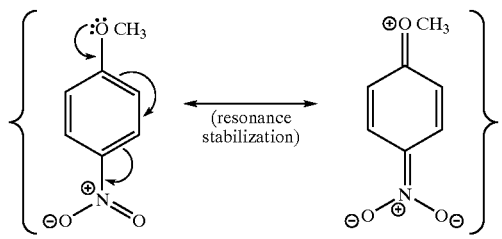

(resonance stabilization)

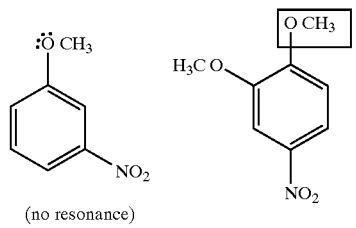

(no resonance)

Selective Cleavage of OMe para to NO2 is possible

| Compound | Eact (Kcal/mole.sec) | |
|---|---|---|
|  | KSCN | KNO$_2$ |
| 4-nitroanisole | 19.17 | 17.908 |
| 3-nitroanisole | 26.64 | 20.36 |

From the foregoing, it will be observed that numerous variations and modifications may be effected without departing from the true spirit and scope of the novel concepts of the invention.

What is claimed is:

1. A method of producing N-acetyl-p-aminophenol in a solvent minimized environment, which comprises contacting a compound of the formula:

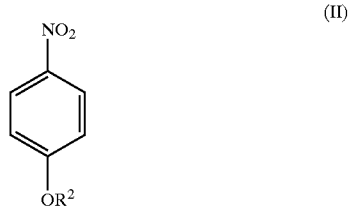

(II)

wherein $R_2$ is —H or a $C_1$–$C_4$ alkyl group with a catalytic amount of a catalyst system comprising (i.) an oxyethylene ether; and (ii.) alkali metal thioacetate for a time sufficient to form N-acetyl-p-aminophenol.

2. The method of claim 1, wherein the oxyethylene ether is a polyethylene glycol or an aryl polyoxyethylene ether of the formula:

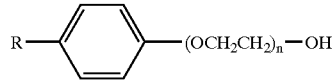

wherein R is an aryl, alkyl or aralkyl group having from 1 to 20 carbon atoms and n has an average integer value between from about 9 to about 150.

3. The method of claim 1, wherein the $R_2$ is —H.

4. The method of claim 3, wherein the equivalent weight ratio of the compound of formula (II):alkali metal thioacetate is approximately 1:1.

5. The method of claim 1, wherein $R_2$ is a $C_1$–$C_4$ alkyl group.

6. The method of claim 5, wherein the equivalent weight ratio of the compound of formula (II):alkali metal thioacetate is approximately 1:3.

7. The method of claim 1, wherein the alkali thioacetate is potassium thioacetate.

\* \* \* \* \*